United States Patent [19]
Du Vosel et al.

[11] Patent Number: 5,328,631
[45] Date of Patent: Jul. 12, 1994

[54] POLYAMINOACIDS AS BUILDERS FOR FORMULATIONS OF DETERGENTS

[75] Inventors: Annick Du Vosel; Franco Francalanci; Paola Maggiorotti, all of Novara, Italy

[73] Assignee: S.R.L. Montedipe, Milan, Italy

[21] Appl. No.: 691,877

[22] Filed: Apr. 26, 1991

[30] Foreign Application Priority Data

Apr. 26, 1990 [IT] Italy ................................ 20145 A/90

[51] Int. Cl.$^5$ ...................... C11D 3/08; C11D 3/386; C11D 3/384
[52] U.S. Cl. ........................ 252/174.23; 252/174.74; 252/175.25; 252/546; 252/527; 562/553; 562/433
[58] Field of Search ............... 252/546, 527, 174.24, 252/174.23, 174.25; 562/553, 433

[56] References Cited

U.S. PATENT DOCUMENTS

| | | | |
|---|---|---|---|
| 4,333,844 | 8/1982 | Duggleby et al. | 252/97 |
| 4,514,185 | 8/1985 | Lee et al. | 8/137 |
| 4,560,492 | 12/1985 | Curry | 252/527 |
| 4,666,738 | 5/1987 | Wixon | 427/214 |
| 4,839,461 | 6/1989 | Boehmke | 528/363 |
| 4,839,461 | 6/1989 | Boehmke | 528/328 |

FOREIGN PATENT DOCUMENTS

| | | |
|---|---|---|
| 0454126 | 4/1991 | European Pat. Off. ........ 252/174.23 |
| 1806502 | 3/1970 | Fed. Rep. of Germany ............ 252/174.24 |
| 3724460 | 2/1988 | Fed. Rep. of Germany ... 252/DIG. 5 |
| 13626672 | 11/1988 | Fed. Rep. of Germany . |
| 1404814 | 4/1975 | United Kingdom . |
| 2160424 | 6/1984 | United Kingdom ....... 252/DIG. 13 |

*Primary Examiner*—Paul Lieberman
*Assistant Examiner*—Kery A. Fries
*Attorney, Agent, or Firm*—Morgan & Finnegan

[57] ABSTRACT

This invention relates to use of polyaminoacids as builders or co-builders in the formulation of detergents. These polyaminoacids, which are highly efficient as complexing agents, have good resistance to heat and stability to pH and are entirely biodegradable, have been chosen among those having the general formula:

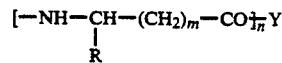

with substituents which are defined in the following description.

The formulations of detergents contain, apart from the above builders, surface active agents, alumina-silicates and additives chosen from neutral salts, enzymes, bleaching agents, stabilizers, anti-foaming agents, perfumes, bactericides.

3 Claims, No Drawings

POLYAMINOACIDS AS BUILDERS FOR FORMULATIONS OF DETERGENTS

FIELD OF THE INVENTION

The present invention concerns the use of polyaminoacids or their derivatives, as builders or co-builders in the formulation of detergents. These products are very efficient as complexing agents, show a good stability to heat and to pH, and are also entirely biodegradable.

BACKGROUND OF THE INVENTION

It is now well-known that products used for detergents are mostly responsible for the presence of phosphorous in water: among these the effect of sodium tripolyphosphate (STPP), used as a builder, has been particularly studied.

It is also well known that many efforts have been made in research to find an alternative to polyphosphates. But the various solutions attempted have not always given satisfactory results in that, when the STPP is removed or decreased, the variations which occur in the final results of the washing process are greater than those which would have been expected because of the sole decrease of the sequestering power of the detergent matrix.

This is due to the fact that it is impossible to find out a product which possesses the multiple characteristics of STPP, i.e. control of water hardness, buffer action, dirt dispersion and prevention of re-depositing.

Among the builders, citric acid and its salts, zeolites, nitryltriacetic acid (NTA) or polymeric polycarboxylic acids are now used.

Citric acid and sodium citrate are the main builders used in detergent liquids as they are the only ones which do not interfere with the enzymes present. Their percentage in these formulations is around 1–2%.

They represent 5% of the total market of builders.

They have the advantage of being entirely biodegradable, non-toxic, of being highly compatible with the other components of detergents and of having an effect of synergism with other builders (for example zeolytes).

Their use is limited by their efficiency. Their effectiveness quickly decreases with the temperature increase (T>50° C.). They have lower sequestering and dispersion power than polyphosphates (STPP).

Zeolytes are used in powder formulations.

As far as their toxic effect on the environment is concerned, these products are acceptable. They do not present any risk for water and do not increase the BOD load in plants for the treatment of waste water, even if, being insoluble. They do leave large quantities of sediments and materials in suspension.

As far as their detergency is concerned, they have a good absorbing capacity with respect to colored substances and pigments given out by fabrics. Their effectiveness as ion exchangers increases with the temperature. On the contrary, their ion exchange kinetics are slow, they have no buffer action and no dispersion power.

They are used in combination with other builders.

Nitrilotriacetic acid (NTA), after being initially accepted as a possible substitute for STPP, was then almost completely abandoned because of the numerous environmental problems involved.

As far as its efficiency as a detergent is concerned, its power as a complexing agent is 1.5 times higher than that of STPP and its performance is almost double in formulations for cold water. It has a better buffer effect, it is a good re-depositing prevention agent. It improves the effectiveness of optical bleaches. It stabilizes foams and perborates. It does not hydrolize during the washing process. It increases the solubility of some anionic surface-active agents (LAS type), and it is compatible with other components. It has the disadvantage of decolorizing colored fabrics based on metal complexes and has the tendency to agglomerate.

The real reason for its being abandoned, however, is due to the high toxicological risks involved in its use.

Its biodegradability is extremely limited, and the slime used for its processing requires a long acclimatation period. The rate of this process seems too slow to be able to keep up with the high fluctuations of NTA concentration, thus preventing its complete removal. The situation becomes worse in the processing of sea water and generally when the water hardness and NTA concentration increase.

The degradation of NTA is very limited also under anaerobic conditions. The above situation can have serious consequences: penetration and pollution of the water-tables damage to phytoplancton which cannot survive NTA concentrations higher than 1000 micrograms/liter with a risk of interrupting the feedingchain. The formation of complexes with the heavy metals present in the sediments, which go back again into solution, increase the risk of genetical changes and tumors.

The most valid polymeric polycarboxylic acids have been proved to be copolymers made up of acrylic acid and maleic anhydride.

These products are good complexing agents, they have a good dispersion and re-depositing prevention capacity, they improve the structure of the detergents by preventing the formation of lumps.

The main problem which limits their use is associated with their lack of biodegradability. It seems that polycarboxylates are accepted in Europe because they are protected by German legislation, for which it is sufficient for builders to be eliminated from water but not necessarily from the environment. This means that products are accepted which are not biodegradable (and thus cannot be eliminated from the environment) but are absorbed into the membranes of bacteria and in this way, eliminated from water.

It is precisely the biodegradability which stimulated further research on an alternative detergency. This brought about the study of copolymers of maleic anhydride and/or acrylic acid with natural substances such as starch or dextrine, copolymers of maleic anhydride and substances capable of introducing allylic and vinylic groups, copolymers of maleic anhydride/ethylene oxide, copolymers of glyoxylic acid/formaldehyde, etc. However results are still far from reaching expectations. At present, most detergents contain between 2 and 4% of polymers, mainly acrylic/maleic polymers combined with other builders.

It is also known (English patent No. 1404814) that polyaminoacids can act as surface-active agents, in that they are obtained through a reaction between polyimidic derivatives and long-chain aliphatic amines. By controlling the type of chain of the latter or the degree of polymerization of the polyimide, it is possible to choose the final characteristics of the polyaminoacid under examination.

However, the products described in the English patent do not seem to have sufficiently high characteristics to enable them to be used diversely or in any specific way that has not been already indicated. These characteristics may be summarized as follows: biodegradability, non-toxicity, no irritating effects, high solubility in water which, together with the detergent properties, determine the applicability and versatility of use in subsequent formulations.

DETAILED DESCRIPTION OF THE INVENTION

Applicants have now discovered that polyaminoacids or their derivatives can be used as builders or co-builders in the formulation of detergents, having excellent properties as complexing agents with respect to calcium and preventing the formation of $CaCO_3$ crystals; the above products are also extremely efficient complexing agents, have a good resistance to heat and stability to pH, they are not toxic, do not irritate and are entirely biodegradable therefore eliminating all environmental problems.

The detergent base, made up of polyaminoacids and anionic and/or non ionic and/or amphoteric surface-active agents can be used with conventional products such as enzymes, bleaching agents, stabilizers, neutral salts, anti-foaming agents, perfumes, bactericides, etc.

Applicants point out that the results are even more surprising in that it is well-known that amino acids such as L-aspartic acid and L-glutamic acid, although having good capacities as complexing agents as regards to transition metal such as Fe, Co and Ni, are not able to form stable complexes with alkali or alkaline earth metals (Angew—Chem. Ind. Ed. Engl. 29 (1990) 1090-1103).

The present invention consequently concerns a group of polyaminoacids and their derivatives having the following general formula (I) which can be used as builders and co-builders.

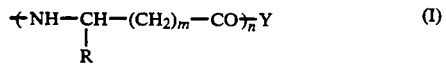

in which, m can be equal to 0, 1, 2; n has a value between 5 and 2000; R can be: H, $CH_3$, COY, $CH_2COY$, $CH_2CH_2COY$, $CH_2CH_2CH_2NHC=(NH_2)NH$, $CH_2SH$, $CH_2CH_2CH(OH)CH_2NH_2$, $CH_2CH(CH_3)_2$, $CH(CH_3)CH_2CH_3$,

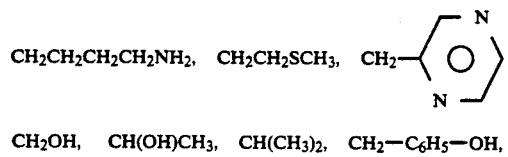

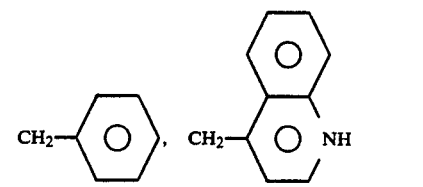

wherein Y can be:

—OZ wherein Z represents H or a $C_1$-$C_{15}$ alkyl radical; or —NZZ' wherein Z and Z' are the same or different from one another, and represent H or a $C_1$-$C_{15}$ alkyl radical.

These amino acids have a molecular weight of between 300 and 200,000.

The products belonging to the above formula (I) can be prepared using the well-known methods for the synthesis and which can be used by all experts in the field, depending on the type of substituents required and the number of carbon atoms.

For example, for m=0, the amino acids, possibly protected, can be reacted with phosgene or its derivatives, thus obtaining the corresponding N-carboxy-anhydrides (ref.: A. J. Domb, E. G. Cravalho and R. Langer; J. Polymer Science part. A Polym. Chem., 1988, 26, 2623 ):

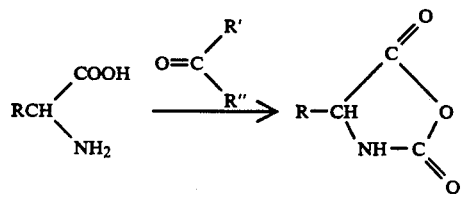

were R has the above meaning; R' and R", either alike or different in the same molecule, can be Cl, $OCCl_3$, OR''' (were R''' can be an alkyl or aryl group having from 1 to 15 carbon atoms).

The N-carboxy-anhydrides thus obtained are polymerized in the presence of bases which act as catalysts (for example amines, or bases made by electrolysis), giving structures of type (I).

Polymers having general formula (I) with m=0, 1, 2, can be obtained by thermal polymerization of amino acids obtaining the corresponding polyamides (ref.: S. W. Fox, K. Harada, JACS, 1958, 80, 2694; S. W. Fox, K. Harada, JACS, 1960, 82, 3715).

Among all possible amino acids having formula (I), those derived from aspartic acid, glutamic acid and their mixtures have proved to be the most effective.

It is therefore possible to formulate detergent compositions with these polyaminoacids (either alone or in mixtures), in percentages of between 5 and 50% by weight, together with, naturally, one or more surface-active agents (10-40%), at least one zeolyte (0.5-70%), and one or more additives chosen from neutral salts, enzymes, bleaching agents, stabilizers, antifoaming agents, perfumes and bactericides.

EXAMPLES

The effectiveness of the present products will be shown herebelow in relation to their activity as Calcium complexing agents through the following non-limiting examples.

Their activity as complexing agents was established by using a selective electrode for ion $Ca^{++}$, coupled with a counter-electrode of calomel.

EXAMPLE 1

The solution of the complexing agent was prepared by adding 51 mg of polyaspartic acid with n=4, to 100 ml of a water solution containing NaCl 1M and buffered at pH 10 ($NH_3$). 1 ml of a solution of $CaCl_2$ 0.1M was added at a constant temperature of 25° C. The residual concentration of $Ca^{++}$ both after 5 and 30 minutes was equal to $7.10^{-4}M$.

EXAMPLE 2

53.46 mg of the amide of the polyaspartic acid with n=4 were added to the above buffered solution. 1 ml of a solution of $CaCl_2$ 0.1M was added at a constant temperature of 25° C. The residual concentration of $Ca^{++}$ both after 5 and 30 minutes was equal to $7.10^{-4}M$.

EXAMPLE 3

52.69 mg of the amide of the polyaspartic acid with n=8 were added to the buffered solution. 1 ml of a solution of $CaCl_2$ 0.1M was added at a constant temperature of 25° C. The residual concentration of $Ca^{++}$ both after 5 and 30 minutes was equal to $2.10^{-4}M$.

EXAMPLE 4

101.52 mg of the polymer of the polyaspartic acid with n>150 were added to the buffered solution. 2 ml of a solution of $CaCl_2$ 0.1M was added at a constant temperature of 25° C. The residual concentration of $Ca^{++}$ after 5 minutes was equal to $6.10^4M$ and after 30 minutes was equal to $3.10^{-5}M$.

EXAMPLE 5

103.88 mg of polyglutamic acid with n>100 were added to the buffered solution. 1 ml of a solution of $CaCl_2$ 0.1M was added at a constant temperature of 25° C. The residual concentration of $Ca^{++}$ after 30 minutes was equal to $10^{-4}M$.

EXAMPLE 6

50 mg of polyaspartic acid with n=4 were added to the buffered solution. 1 ml of a solution of $CaCl_2$ was added at a constant temperature of 60° C. The concentration of $Ca^{++}$ both after 5 and 30 minutes was equal to $5.10^{-4}M$.

EXAMPLE 7

49 mg of the amide of polyaspartic acid with n=4 were added to the buffered solution. 1 ml of a solution of $CaCl_2$ 0.1M was added at a constant temperature of 60° C. The final concentration of $Ca^{++}$ after 30 minutes was equal to $5.10^{-4}M$.

EXAMPLE 8

50 mg of the amide of polyaspartic acid with n=8 were added to the solution. 1 ml of a solution of $CaCl_2$ 0.1M was added at a constant temperature of 60° C. The concentration of $Ca^{++}$ after 30 minutes decreased to $3.10^{-4}M$.

EXAMPLE 9

49 mg of polyaspartic acid with n>150 were added to the solution. 1 ml of a solution of $CaCl_2$ 0.1M was added at a constant temperature of 60° C. The concentration of $Ca^{++}$ after 30 minutes decreased to $1.10^{-4}M$.

EXAMPLE 10

51 mg of polyglutamic acid with n>100 were added to the solution. 1 ml of a solution of $CaCl_2$ 0.1M was added at a constant temperature of 60° C. The residual concentration of $Ca^{++}$ after 30 minutes was equal to $2.10^{-4}M$.

Washing tests were carried out on formulations containing the above polyaminoacids as builders or co-builders, as described below, using as a comparison, a similar system with the exception that the polyaminoacids were substituted by acrylic/maleic copolymers.

In these formulations, the components are present in quantities included in the following ranges:
5-50% by weight of polyaminoacids
10-40% by weight of anionic and/or non ionic and/or amphoteric surface-active agents
5-50% by weight of sodium alumino-silicates
0.5-70% by weight of neutral salts, enzymes, bleaching agents, stabilizers, anti-foaming agents, perfumes, bactericides, water.

EXAMPLE 11

0% Polyaminoacids
12% alkylbenzenesulfonates ($C_9$-$C_{15}$)
25% sodium aluminosilicates
25% sodium perborate
23% sodium sulfate
5% water

EXAMPLE 12

15% polyaminoacids
20% ethoxylated n-alcohols ($C_{12}$-$C_{16}$) (n=10-15)
20% sodium aluminosilicates
20% sodium perborate
20% sodium sulfate
5% water

EXAMPLE 13 comparison sample

10% akrylic/maleic copolymer
12% alkylbenzenesulfonates ($C_9$-$C_{15}$)
25% sodum aluminosilicates
25% sodium perborate
23% sodium sulfate
5% water As pointed out in the introduction, acrylic acid/maleic anhydride copolymers are good complexing agents, have a high dispersion and precipitation-preventing power, and also prevent the formation of lumps.

Furthermore, the use of builders according to the present invention (formulations corresponding to examples 11 and 12) produce compositions which have detergent properties at least equal to those containing the above-mentioned copolymers. The degree of whiteness obtained is in fact never inferior to that of compositions known to date.

However, the builders used in the detergent formulations in accordance with the present invention, are substantially completely biodegradable, which represents a definite advantage over other known detergent formulations.

Washing tests were also carried out in a washing-machine with a detergent formulation containing zeolyte both in the presence of and without a polyaminoacid.

EXAMPLE 14

The tests were made with the following formulation:

| | |
|---|---|
| Surface-active agent | 14.0% |
| Zeolyte | 27.0% |
| Carbonate | 10.0% |
| Enzyme | 0.4% |
| Polyaspartate | 0% |
| Sulfate | 22% |
| Perborate 4 | 20.0% |
| Silicate 2 | 3.0% |

-continued

| | |
|---|---|
| Water | approx. 3.6% |
| Working conditions: | |
| 30° | |
| 90° C. | |
| Without CMC (carboxymethylcellulose) | |
| 3-6 washing cycles | |

The actual performance during the washing process was evaluated as follows:

A) DETERGENCY

The study was carried out using a standard dirty strip type EMPA 103.

The following observations were made:
- there were no negative influences; behavior in the presence of the polyaminoacid was better than it was with the zeolyte alone;
- results were particularly positive in the case of cocoa and blood/milk/China ink stains;
- the surface-active agent has an effect of synergism thus improving the overall cleansing action.

B) SECONDARY EFFECTS OF THE WASHING PROCESS (CRUST FORMATION)
- the amount of crusting decreases with respect to when zeolyte alone is used.
- as the complexing power is low, it can be assumed that it has a good dispersion effect for the crusting (and also for the dirt);
- even better results are expected (with respect to zeolyte alone) if 15 washing cycles are carried out.

The detergency activity of polyaspartate is presumably brought about through its high dispersion capacity of both the dirt and crusting salts (it does not allow these to deposit). Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. A detergent formulation containing 10 to 40% by weight of at least one surface active agent, from 5 to 50% of weight of at least one sodium aluminosilicate, from 0.5 to 70% by weight of at least one additive chosen from neutral salts, enzymes, bleaching agents, stabilizers, anti-foaming agents, perfumes, bactericides and from 5 to 50% by weight of a builder or cobuilder which is at least one polyamino acid chosen from those having the formula:

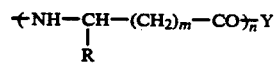

in which m can be 1 or 2; n is between 100 and 2000; R is a radical chosen from: H, $CH_3$, COY, $CH_2COY$, $CH_2CH_2COY$, $CH_2CH_2CH_2NHC=(NH_2)NH$ $CH_2SH$, $CH_2CH_2CH(OH)CH_2NH_2$, $CH_2CH(CH_3)_2$, $CH(CH_3)CH_2CH_3$, $CH_2CH_2CH_2CH_2NH_2$, $CH_2CH_2SCH_3$,

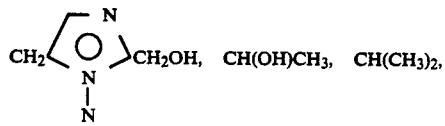

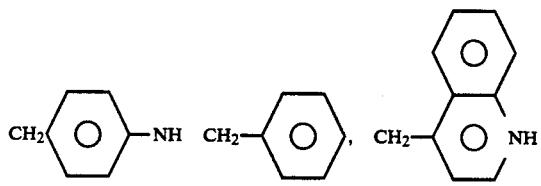

wherein Y can be:
—OZ wherein Z represents H or a $C_1$–$C_{15}$ alkyl radical; or —NZZ' wherein Z and Z' are the same or different from one another, and represent H or a $C_1$–$C_{15}$ alkyl radical.

2. A detergent formulation according to claim 1, wherein the builder or cobuilder is polyaspartic acid.

3. A detergent formulation according to claim 1, wherein the builder or cobuilder is polyglutamic acid.